United States Patent
Hori et al.

(10) Patent No.: US 7,029,693 B2
(45) Date of Patent: Apr. 18, 2006

(54) PERCUTANEOUSLY ABSORPTIVE PREPARATION

(75) Inventors: Mitsuhiko Hori, Ibaraki (JP); Kensuke Matsuoka, Ibaraki (JP); Kenjiro Minomi, Ibaraki (JP); Yoshihisa Nakano, Ibaraki (JP)

(73) Assignee: Nitto Denko Corporation, Ibaraki (JP)

(*) Notice: Subject to any disclaimer, the term of this patent is extended or adjusted under 35 U.S.C. 154(b) by 427 days.

(21) Appl. No.: 09/946,889

(22) Filed: Sep. 5, 2001

(65) Prior Publication Data
US 2002/0106401 A1 Aug. 8, 2002

(30) Foreign Application Priority Data
Sep. 5, 2000 (JP) .............................. 2000-268899

(51) Int. Cl.
*A61K 9/70* (2006.01)
*A01N 25/34* (2006.01)
(52) U.S. Cl. .................... 424/449; 424/402; 424/443
(58) Field of Classification Search ............... 424/402, 424/443, 449
See application file for complete search history.

(56) References Cited

U.S. PATENT DOCUMENTS

| | | | | |
|---|---|---|---|---|
| 4,645,502 A | * | 2/1987 | Gale et al. | 604/896 |
| 4,855,294 A | * | 8/1989 | Patel et al. | 514/212 |
| 5,124,157 A | * | 6/1992 | Colley et al. | |
| 5,186,939 A | | 2/1993 | Cleary et al. | |
| 5,352,457 A | | 10/1994 | Jenkins | |
| 5,494,680 A | * | 2/1996 | Peterson | |
| 5,585,111 A | | 12/1996 | Peterson | |
| 6,183,853 B1 | * | 2/2001 | Exsted | |
| 6,376,032 B1 | * | 4/2002 | Clarke et al. | |

OTHER PUBLICATIONS

The American Heritage Dictionary, 2nd. Ed., Houghton Mifflin Co., Boston (1982).*

* cited by examiner

*Primary Examiner*—Thurman K. Page
*Assistant Examiner*—Humera N. Sheikh
(74) *Attorney, Agent, or Firm*—Leydig, Voit & Mayer, Ltd.

(57) ABSTRACT

A percutaneously absorptive preparation is provided, which preparation having a support and an adhesive layer having a release-controlling layer, which is formed at least on one side of the support, wherein the adhesive layer contains an adhesive and 0.5–60 wt % of a drug except 1,2-ethanediol derivatives.

7 Claims, 1 Drawing Sheet

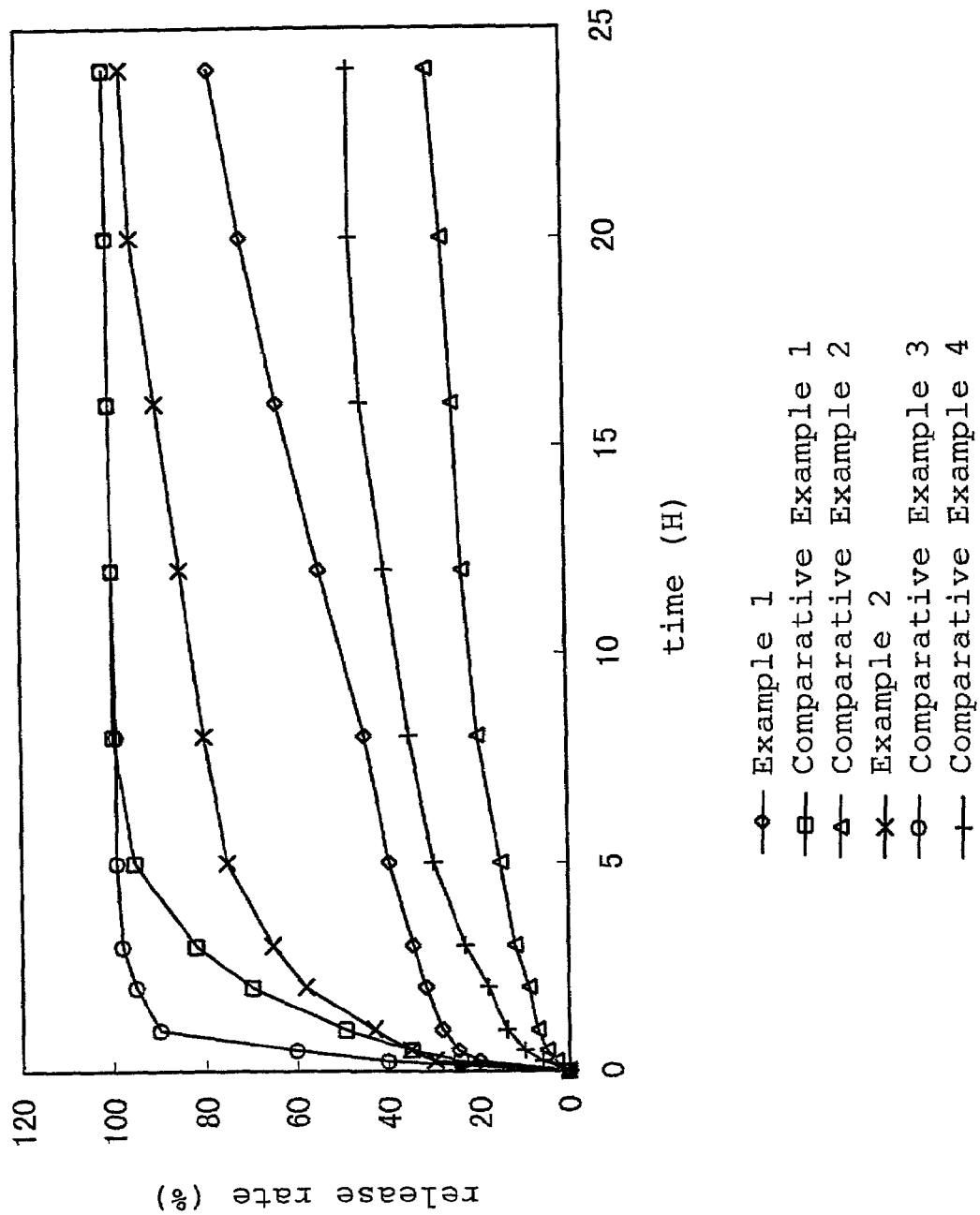

US 7,029,693 B2

PERCUTANEOUSLY ABSORPTIVE PREPARATION

TECHNICAL FIELD OF THE INVENTION

The present invention relates to a percutaneously absorptive preparation containing a specific amount of a drug except 1,2-ethanediol derivatives, which allows sustained percutaneous absorption of the drug into the body and which suppresses irritation to the skin caused by the drug.

BACKGROUND OF THE INVENTION

For administration of drugs, medical adhesive sheet type preparations, so-called percutaneously absorptive preparations, have been drawing attention in recent years, in view of the feasibility of medication, easiness of controlling medication and the like, wherein the preparation is applied to the skin by the action of an adhesive.

Inherently, however, the skin functions as a barrier system to protect body against the outer environment and powerfully blocks the body from the invasion of foreign substances. For a pharmacological effect of a drug for percutaneous administration to be fully exerted, a percutaneously absorptive preparation having skin permeability overriding such barrier function needs to be developed.

In an attempt to improve skin permeability, a percutaneous absorption promoter is frequently added to an adhesive; iontophoresis is utilized wherein an ionized drug is percutaneously absorbed by conducting the skin; a drug is physically absorbed percutaneously by phonophoresis using ultrasonication; and the like.

On the other hand, many compounds have been reported to cause irritation to the skin when applied to percutaneous absorption. Because percutaneously absorptive preparations aim at percutaneous absorption of a drug into the body, percutaneous absorption of a drug, that may cause irritation to the skin, requires sufficient percutaneous absorption of the drug by the body at a concentration of the level free of irritation to the skin, which means the preparation should have conflicting actions.

SUMMARY OF THE INVENTION

It is therefore an object of the present invention to provide a percutaneously absorptive preparation which is capable of sustained percutaneous absorption of a drug into the body to sufficiently exert a desired pharmacological effect, and which is capable of suppressing irritation to the skin caused by the drug.

According to the present invention, an adhesive layer having a release-controlling layer is formed on at least one side of a support to allow control of the release amount and the release rate of a drug contained in the adhesive layer, thereby to realize sustained percutaneous absorption of a drug in an amount sufficient to express a pharmacological effect, and to provide a percutaneously absorptive preparation associated with less irritation to the skin due to the drug.

Therefore, the present invention provides the following.

(1) A percutaneously absorptive preparation comprising a support and an adhesive layer having a release-controlling layer, which is formed at least on one side of the support, wherein the adhesive layer contains an adhesive and 0.5–60 wt % of a drug except 1,2-ethanediol derivatives.

(2) The percutaneously absorptive preparation of the abovementioned (1), wherein the adhesive is at least one member selected from the group consisting of an acrylate adhesive comprising, as a main component, a polymer containing, as a polymerization component, $C_{2-18}$ alkyl (meth)acrylate in a proportion of not less than 40 wt %; a rubber adhesive comprising at least one member selected from polyisobutylene, polyisoprene and styrene-diene-styrene copolymer as a main component; and a silicone adhesive comprising polyorganosiloxane containing a dimethylsiloxane unit as a main component.

(3) The percutaneously absorptive preparation of the abovementioned (1), wherein the adhesive layer contains at least one organic liquid component selected from the group consisting of glycols, fats and oils, fatty acids, alcohols and fatty acid esters.

(4) The percutaneously absorptive preparation of the abovementioned (1), wherein the adhesive is a rubber adhesive comprising polyisobutylene as a main component and the adhesive layer further contains a lower alkyl ester of a higher fatty acid.

(5) The percutaneously absorptive preparation of the abovementioned (1), wherein the release-controlling layer is a porous plastic film.

(6) The percutaneously absorptive preparation of the abovementioned (5), wherein the porous plastic film is made from a high molecular weight polyethylene.

(7) The percutaneously absorptive preparation of the abovementioned (5) or (6), wherein the porous plastic film has a porosity of 20–60%.

(8) The percutaneously absorptive preparation of the abovementioned (1), wherein the adhesive layer having a release-controlling layer has a laminate structure consisting of adhesive layer A/release-controlling layer/adhesive layer B from the support side.

(9) The percutaneously absorptive preparation of the abovementioned (8), wherein the adhesive layer B has a drug content of not more than 200 $\mu g/cm^2$.

BRIEF DESCRIPTION OF THE DRAWINGS

FIG. 1 is a graph showing the results of an underwater release test in Test Example 1.

DETAILED DESCRIPTION OF THE INVENTION

The percutaneously absorptive preparation of the present invention contains a support and an adhesive layer having a release-controlling layer, which is formed at least on one side of the support, wherein the adhesive layer contains an adhesive and a drug except 1,2-ethanediol derivatives.

The drug to be used in the present invention may be any but 1,2-ethanediol derivatives, and is determined according to the object of therapy. Examples thereof include corticosteroids (e.g., hydrocortisone, prednisolone, beclometasone propionate, flumethasone, triamcinolone, triamcinolone acetonide, fluocinolone, fluocinolone acetonide, fluocinolone acetonide acetate, clobetasol propionate etc.), analgesic inflammatory agents (e.g., acetaminophen, mefenamic acid, flufenamic acid, indomethacin, 1-menthol, camphor, sulindac, fenbufen, phenylbutazone, ibuprofen, tolmetin sodium, diclofenac, diclofenac sodium, alclofenac, oxyphenbutazone, naproxen, flurbiprofen, ketoprofen, salicylic acid, methyl salicylate etc.), hypnosedatives (e.g., phenobarbital, amobarbital, cyclobarbital, lorazepam, haloperidol etc.), tranquilizers (e.g., fluphenazine, thioridazine, diazepam, flunitrazepam, chlorpromazine etc.), antihypertensive agents (e.g., clonidine, clonidine hydrochloride, pindolol, propranolol (hydrochloride), bupranolol, indenolol, bucumorol, nifedipine etc.), hypotensive diuretics (e.g., hydrochlorothiazide, bendroflumethiazide, cyclopenthiazide etc.), antibiotics (e.g., penicillin, tetracycline, oxytetracycline, fradiomycin sulfate, erythromycin, chloramphenicol etc.), anesthetics (e.g., lidocaine, benzocaine, ethyl aminobenzoate etc.), antibacterial agents (e.g., benzalkonium chloride, nitrofurazone, nystatin, acetosulfamin, clotrimazole etc.), antifungus agents (e.g., pentimycin, amphotericin B, pyrrolnitrin, clotrimazole etc.), vitamins (e.g., vitamine A, ergocalciferol, cholecalciferol, octotiamine, riboflavin butyrate etc.), coronary vasodilating agents (e.g., nitroglycerin, nitroglycol, isosorbide nitrate etc.), antihistaminics (e.g., diphenhydramine (hydrochloride), chlorpheniramine etc.), antitussives (e.g., dextromethorphan, terbutaline, ephedrine, ephedrine hydrochloride etc.), sex hormones (e.g., progesterone, estradiol etc.), antidepressants (e.g., imipramine (hydrochloride), amitriptyline hydrochloride etc.), cerebral circulation improving agents, antiemetic drugs (e.g., metoclopramide, domperidone etc.), antitumor agents (e.g., 5-fluorouracil etc.), antiepileptics (e.g., nitrazepam, meprobamate, clonazepam, sodium valproate etc.), anti-vertigo drugs (e.g., betahistine etc.) and the like. These drugs may be used alone or in combination.

The above-mentioned 1,2-ethanediol derivatives, that are not to be used in the present invention, have the following formula (I):

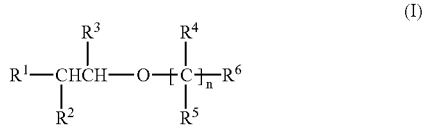

wherein $R^1$ is an optionally substituted heterocyclic group, $R^2$ is a hydrogen atom, a lower alkyl group, a lower alkoxy group or an optionally protected hydroxyl group, $R^3$ is a hydrogen atom or a lower alkyl group, $R^4$ and $R^5$ in number n may be the same or different and each is a hydrogen atom or a lower alkyl group, $R^6$ is an optionally substituted amino group or a nitrogen-containing heterocyclic group, or an ammonio group, and n is an integer of 0–6.

In the above-mentioned formula (I), each symbol means the following unless otherwise specifically indicated.

The halogen atom means a fluorine atom, chlorine atom, bromine atom or iodine atom.

The lower alkyl group means $C_{1-6}$ alkyl group such as methyl, ethyl, n-propyl, isopropyl, n-butyl, isobutyl, tert-butyl, pentyl and hexyl.

The lower alkenyl group means $C_{2-6}$ alkenyl group such as vinyl, propenyl, butenyl, pentenyl and hexenyl.

The lower alkenyloxy group means $C_{2-6}$ alkenyl-O— group.

The cycloalkyl group means $C_{3-6}$ cycloalkyl such as cyclopropyl, cyclobutyl, cyclopentyl and cyclohexyl.

The lower alkoxy group means $C_{1-6}$ alkyl-O— group.
The lower alkylthio group means $C_{1-6}$ alkyl-S— group.
The aryl group means phenyl, naphthyl, indanyl or indenyl.
The aryloxy group means aryl-O— group.
The ar(lower)alkyl group means ar($C_{1-4}$)alkyl group such as benzyl, diphenylmethyl, trityl and phenethyl.
The ar(lower)alkenyl group means ar($C_{2-6}$)alkenyl group such as styryl, cinnamyl and the like.
The ar(lower)alkoxy group means ar($C_{1-4}$)alkyl-O— group.

The ar(lower)alkylthio group means ar($C_{1-4}$)alkyl-S— group.
The lower alkylenedioxy group means $C_{1-4}$ alkylenedioxy group such as methylenedioxy and ethylenedioxy.
The lower acyl group means $C_{1-6}$ alkyl-CO— group such as formyl, acetyl and butyryl.
The aroyl group means aryl-CO— group.
The lower alkylsulfonyl group means $C_{1-6}$ alkyl-$SO_2$— group.
The ar(lower)alkylsulfonyl group means ar($C_{1-6}$)alkyl-$SO_2$— group.
The arylsulfonyl group means aryl-$SO_2$— group.
The lower alkylsulfonyloxy group means $C_{1-6}$ alkyl-$SO_2$—O— group.
The arylsulfonyloxy group means aryl-$SO_2$—O— group.
The arylsulfonylamino group means aryl-$SO_2$NH— group.
The lower alkylsulfonylamino group means $C_{1-6}$ alkyl-$SO_2$NH— group.
The di-lower alkylamino group means di-$C_{1-6}$ alkylamino group.
The ammonio group means tri-$C_{1-6}$ alkylammonio group such as trimethylammonio and triethylammonio.

The nitrogen-containing heterocyclic group means a heterocyclic group of a 5-membered or 6-membered fused ring or bridged ring, containing, as a hetero atom forming a ring, one or more nitrogen atoms and one or more oxygen atoms or sulfur atoms, which is exemplified by pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, thiazolyl, tetrazolyl, thiadiazolyl, pyrrolinyl, imidazolinyl, imidazolidinyl, pyrazolinyl, pyrazolidinyl, purinyl and indazolyl.

The heterocyclic group means the above-mentioned nitrogen-containing heterocyclic group, or a heterocyclic group of a 5-membered or 6-membered fused ring or bridged ring, containing, as a hetero atom forming a ring, one or more oxygen atoms and/or sulfur atoms, which is exemplified by furyl, thienyl, benzofuryl, benzothienyl, isobenzofuranyl, pyranyl, chromenyl, chromanyl, benzopyranyl, xanthinyl, thiopyranyl, thianthrenyl, phenoxanthinyl and the like.

The heterocyclic carbonyl group means heterocycle-CO— group.

The substituent of the "optionally substituted heterocyclic group" at $R^1$ of the formula (I) is exemplified by halogen atom; optionally substituted, amino group, lower alkyl group, aryl group, ar(lower)alkyl group, lower alkoxy group, ar(lower)alkoxy group, aryloxy group, carbamoyloxy group, lower alkylthio group, lower alkenyl group, lower alkenyloxy group, ar(lower)alkylthio group, ar(lower)alkylsulfonyl group, arylsulfonyl group, lower alkylsulfonylamino group, arylsulfonylamino group and heterocyclic group; protected amino group; optionally protected hydroxyl group; nitro group; oxo group; and lower alkylenedioxy group, which substituents may be used singly or in combination.

The substituent of the "optionally substituted, lower alkyl group, aryl group, ar(lower)alkyl group, lower alkoxy group, ar(lower)alkoxy group, aryloxy group, carbamoyloxy group, lower alkylthio group, lower alkenyl group, lower alkenyloxy group, ar(lower)alkylthio group, ar(lower)alkylsulfonyl group, arylsulfonyl group, lower alkylsulfonylamino group, arylsulfonylamino group and heterocyclic group" as the substituent of the "optionally substituted heterocyclic group" at $R^1$ of the formula (I) and the substituent of the "optionally substituted nitrogen-containing heterocyclic group" at $R^6$ of the formula (I) are exemplified by halogen atom, optionally protected hydroxyl group, protected carboxyl group, optionally protected amino group, lower alkyl group optionally substituted with optionally protected hydroxyl group, aryl group optionally substituted with halogen atom, aroyl group optionally substituted with halogen atom, lower alkoxy group optionally substituted with lower alkoxy group, lower acyl group, ar(lower)alkyl group, ar(lower)alkenyl group, heterocyclic group, heterocyclic carbonyl group, oxo group, lower alkylsulfonyl group and arylsulfonyl group, which substituents may be used singly or in combination.

The substituent of the "optionally substituted amino group" as the substituent of the "optionally substituted heterocyclic group" at $R^1$ of the formula (I) and the substituent of the "optionally substituted amino group" at $R^6$ of the formula (I), are exemplified by optionally protected hydroxyl group, lower alkyl group optionally substituted by optionally protected hydroxyl group and/or protected carboxyl group, cycloalkyl group, aryl group, lower acyl group, ar(lower)alkyl group, heterocyclic group, heterocyclic carbonyl group optionally substituted by oxo group, adamantyl group, lower alkylsulfonyl group and arylsulfonyl group, which substituents may be used singly or in combination.

The protecting group of the "optionally protected hydroxyl group" at $R^2$ of the formula (I), the "protected amino group" and "optionally protected hydroxyl group" as the substituent of the "optionally substituted heterocyclic group" at $R^1$ of the formula (I), and the "optionally protected hydroxyl group", "protected carboxyl group", "optionally protected amino group", "optionally protected hydroxyl group" of "lower alkyl group optionally substituted by optionally protected hydroxyl group", and the "protected carboxyl group" of the "lower alkyl group optionally substituted by protected carboxyl group", all as the substituent of the "optionally substituted amino group or nitrogen-containing heterocyclic group" at $R^6$ of the formula (I) may be typical protecting groups of hydroxyl group, carboxyl group and amino group described in "Protective Groups in Organic Synthesis" [Theodra W. Green (1991), John Wiley & Sons. Inc.]. Particularly, the protecting group of hydroxyl group is, for example, lower alkyl group, lower acyl group, 2-tetrahydropyranyl group, or ar(lower)alkyl group such as optionally substituted benzyl.

When the drug to be used in the present invention can form a salt, it may be a free form or a pharmaceutically acceptable salt. Examples of the pharmaceutically acceptable salt include salts with an acid, such as inorganic acids (e.g., hydrochloric acid, hydrobromic acid, sulfuric acid, phosphoric acid and the like); organic acids (e.g., carboxylic acids such as formic acid, acetic acid, oxalic acid, succinic acid, fumaric acid, maleic acid, lactic acid, malic acid, tartaric acid, aspartic acid etc., sulfonic acids such as methanesulfonic acid, benzenesulfonic acid, p-toluenesulfonic acid, naphthalenesulfonic acid etc. and the like, and base salts such as sodium salt, ammonium salt and the like.

In the present invention, a pharmaceutically acceptable salt may be liberated in an adhesive layer by adding a liberating agent of the salt. Examples of the liberating agent include a base such as sodium hydroxide, potassium hydroxide, triethylamine, tetraethylammonium, ammonia, sodium caprylate and the like, and acids such as hydrochloric acid, succinic acid, acetic acid and the like. For percutaneous absorption, the percutaneous absorption property of the drug to be contained in the adhesive layer is in the order of free form of the drug>drug liberated in adhesive layer>pharmaceutically acceptable salt of the drug.

The drug to be used in the present invention is contained in the adhesive layer in a proportion of 0.5–60 wt %, preferably 1–30 wt %. When the content is less than 0.5 wt %, it is difficult to have sufficient amount of the drug absorbed for exertion of a pharmacological effect. Conversely, when it exceeds 60 wt %, the adhesive layer shows lower adhesion to the skin and cannot ensure adhesion to the skin or an effect from an increased amount of the drug for exerting a pharmacological effect, which is economically disadvantageous.

The adhesive to be contained in the adhesive layer in the present invention is an adhesive plaster which adheres to the skin, permits percutaneous administration of the drug contained in the adhesive layer from the skin surface, and which shows adhesiveness at normal temperature.

As such adhesive, medical adhesives that do not cause irritation to the skin and the like upon application to the skin are used, such as acrylic adhesive, natural rubber adhesive, synthetic rubber adhesive (containing, as a main component, synthetic rubber component such as synthetic isoprene rubber, polyisobutylene rubber, styrene/butadiene rubber, styrene/isoprene/styrene rubber, styrene/butadiene/styrene rubber and the like), silicone adhesive, vinyl ester adhesive, vinyl ether adhesive and the like are preferable.

Of the above-mentioned adhesives, at least one adhesive selected from the group consisting of acrylate adhesive containing, as a main component, a polymer containing $C_{2-18}$ alkyl (meth)acrylate in a proportion of not less than 40 wt % as a polymerization component; rubber adhesive containing, as a main component, at least one of polyisobutylene, polyisoprene and styrene-diene-styrene copolymer; and silicone adhesive containing, as a main component, polyorganosiloxane having a dimethylsiloxane unit is preferably used in view of the stability of quality and easiness of control of adhesive property. Particularly, a rubber adhesive containing polyisobutylene as a main component is preferable in view of the drug stability.

The above-mentioned acrylate adhesive is not subject to any particular limitation as long as it has the above-mentioned composition. In view of easy control of the adhesive property and the like, a copolymer obtained by copolymerizing 50–98 wt % of one or more kinds of $C_{2-18}$ alkyl (meth)acrylate, and 2–50 wt % of one or more kinds of copolymerizable monomers is preferable.

Examples of the above-mentioned $C_{2-18}$ alkyl (meth) acrylate include esters obtained from primary, secondary or tertiary alcohol containing an alkyl group having 2 to 18, preferably 4 to 12, carbon atoms, and acrylic acid or methacrylic acid.

Examples of the above-mentioned copolymerizable monomer include monomers having at least one unsaturated double bond involved in the copolymerization reaction and a functional group on the side chain, such as carboxyl group [e.g., (meth)acrylic acid, itaconic acid, maleic acid, maleic anhydride etc.]; hydroxyl group [e.g., hydroxyethyl (meth)acrylate, hydroxypropyl (meth)acrylate etc.]; sulfo group [e.g., styrenesulfonic acid, allylsulfonic acid, sulfopropyl (meth)acrylate, (meth)acryloyloxynaphthalene sulfonic acid, acrylamide methylpropanesulfonic acid etc.]; amino group [e.g., aminoethyl (meth)acrylate, dimethylaminoethyl (meth)acrylate, tert-butylaminoethyl (meth)acrylate etc.]; amide group [e.g., (meth)acrylamide, dimethyl(meth)acrylamide, N-butyl acrylamide, N-methylol(meth)acrylamide, N-methylolpropane(meth)acrylamide etc.]; alkoxyl group [e.g., methoxyethyl (meth)acrylate, ethoxyethyl (meth)acrylate, methoxyethylene glycol (meth)acrylate, methoxydiethylene glycol (meth)acrylate, methoxypolyethylene glycol (meth)acrylate, tetrahydrofurfuryl (meth)acrylate etc.] and the like.

Examples of copolymerizable monomer other than the above-mentioned include (meth)acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrazine, vinylpyrrole, vinylimidazole, vinylcaprolactam, vinyloxazole, vinylmorpholine and the like.

It is possible to use one or more kinds of the above-mentioned copolymerizable monomers. In view of the adhesiveness and cohesion as adhesive properties, releasing property of the drug contained in an adhesive layer, and the like, at least one kind of carboxyl group-containing monomer and hydroxyl group-containing monomer is copolymerized in a proportion of 1–50 wt %, particularly 3–20 wt %, and where necessary, other copolymerizable monomers exemplified above, such as vinyl monomer (e.g., vinyl acetate and N-vinyl-2-pyrrolidone) are preferably copolymerized in a proportion of not more than 40 wt %, particularly not more than 30 wt %.

Examples of the acrylic adhesive include a copolymer made from 2-ethylhexyl acrylate and acrylic acid, a copolymer made from 2-ethylhexyl acrylate and 2-hydroxyethyl acrylate, a copolymer made from 2-ethylhexyl acrylate and 2-methoxyethyl acrylate and vinyl acetate, a copolymer made from 2-ethylhexyl acrylate and vinylpyrrolidone, a copolymer made from 2-ethylhexyl acrylate and vinylpyrrolidone and acrylic acid, and the like.

According to the present invention, the adhesive layer preferably contains at least one organic liquid component selected from the group consisting of glycols, fats and oils, fatty acids, alcohols and fatty acid esters. When an adhesive layer contains the organic liquid component, adhesion to the skin, skin permeability of the drug, and reduction of irritation to the skin upon peeling off and the like can be further improved. In other words, skin permeability of the drug can be improved, the adhesive preparation gives a soft feel upon adhesion to the skin because the organic liquid component compatible with the adhesive plasticizes the adhesive layer, suitable cohesive force can be imparted by crosslinking treatment, and irritation to the skin upon peeling off after use can be reduced.

Examples of the above-mentioned glycols include ethylene glycol, diethylene glycol, triethylene glycol, polyethylene glycol, propylene glycol, polypropylene glycol and the like. Those having a high molecular weight, such as polyethylene glycol, polypropylene glycol and the like, preferably has a weight-average molecular weight of 200–1000.

Examples of the above-mentioned fats and oils include olive oil, castor oil, squalene, squalane, orange oil, mineral oil and the like.

Examples of the above-mentioned fatty acids include monocapric acid, oleic acid, caprylic acid, lauric acid, undecylenic acid, isostearic acid, linoleic acid and the like, that have the total number of carbons of 6 to 20.

Examples of the above-mentioned alcohols include alcohols other than the above-mentioned glycols, which have 1 to 20 carbon atoms, such as ethanol, methanol, octyl alcohol, ethoxylated stearyl alcohol, 1,3-butanediol, decyl alcohol, cineole, oleyl alcohol and the like.

Examples of the above-mentioned fatty acid esters include isopropyl myristate, diethyl sebacate, ethyl oleate, diethyl phthalate, diisopropyl adipate, propylene glycol fatty acid ester, lauryl nicotinate, lauryl pyrrolidone carboxylate and the like, that have the total number of carbons of 6 to 20.

The content of the above-mentioned organic liquid component is preferably 3–200 parts by weight, more preferably 10–180 parts by weight, particularly preferably 20–100 parts by weight, per 100 parts by weight of the adhesive. When the content of the organic liquid component is too small, the effect by the addition cannot be expected. When it is too high, the adhesive layer is plasticized too much, which in turn results in lower cohesive force. This has a consequence that a crosslinking treatment cannot avoid glue remainder on the skin surface and that the irritation to the skin upon peeling off may be increased.

As mentioned above, the use of a rubber adhesive containing polyisobutylene as a main component is preferable in the present invention for the drug stability. In this case, a lower alkyl ester of a higher fatty acid is preferably contained as the above-mentioned organic liquid component.

Specifically, a suitable combination of a high molecular weight polyisobutylene having a viscosity-average molecular weight (Mv) of 900,000–2,100,000, a moderate molecular weight polyisobutylene having an Mv of 10,000–200,000, and a low molecular weight polyisobutylene having an Mv of 500–4,000 as the polyisobutylene is preferable for the balance of the adhesive properties (adhesive force, cohesive force, tack and the like) in applying to the skin.

The mixing ratio of the above-mentioned respective polyisobutylenes is 10–80 wt %, particularly 20–70 wt %, of a high molecular weight polyisobutylene, 0–90 wt %, particularly 10–80 wt % of a moderate molecular weight polyisobutylene, and 0–80 wt %, particularly 0–60 wt %, of a low molecular weight polyisobutylene is preferable. By containing each polyisobutylene in the above-mentioned range, the obtained polyisobutylene adhesive comes to have superior balance of adhesive properties, which enables effective realization of percutaneous absorption of a drug according to the present invention.

Examples of the lower alkyl ester of higher fatty acid as the organic liquid component include esterification products of higher fatty acids having 10 to 14 carbon atoms, such as isopropyl myristate, diethyl sebacate and the like, and lower alcohols having 1 to 3 carbon atoms. The content of these organic liquid components is preferably 3–80 parts by weight, particularly 10–40 parts by weight, per 100 parts by weight of a rubber adhesive containing polyisobutylene as a main component. The content in this range reduces irritation to the skin due to the drug and improves percutaneous absorption of the drug.

According to the present invention, moreover, a tackifier may be used along with the adhesive where necessary to increase the viscosity of the adhesive layer. Examples of the tackifier include rosin, rosin derivative, polyterpene resin, chromanindene resin, petroleum resin, terpene-phenol resin and the like.

In the present invention, the adhesive layer may contain an additive, where necessary, such as antioxidants, pigments, fillers, percutaneous absorption promoters, stabilizers for drug, solubilizing agents for drug, insolubilizing agents for drug and the like. Generally, these additives are contained in a proportion of generally about 0.1–50 wt %, preferably 1–10 wt %, of the adhesive layer.

According to the present invention, the adhesive layer contains a release-controlling layer. The release-controlling layer aims at controlling the release amount and the release rate of the drug contained in the adhesive layer when it is released from the surface of the adhesive layer to the skin surface in contact with the layer due to the spreading diffusion, as well as functioning as a barrier against free diffusion.

The adhesive layer containing a release-controlling layer in the present invention has a laminate structure of, for example, adhesive layer A/release-controlling layer/adhesive layer B, the order being from the support side. In this structure, the compositions of the adhesive layer A and adhesive layer B may be the same or different, wherein the kind and amount to be contained of the adhesive, organic liquid component and the like, and the amount to be add of the drug may vary.

The above-mentioned release-controlling layer may be paper, nonwoven fabric, woven fabric, plastic film having pores and the like, and may be a plastic film without pores (e.g., polyethylene film, polypropylene film, ethylene/vinyl acetate copolymer film) if the drug can dissolve therein. When a non-porous plastic film is used, the release rate of the drug from the adhesive layer A may become slow, degrading the effective utilization rate of the drug in the adhesive layer A, and the film swells due to the organic liquid component, thus producing wrinkles. It is preferable, therefor, that a plastic film having pores, particularly porous plastic film, be used. While the thickness of the porous plastic film is not particularly limited, it is preferably not more than 100 μm to decrease uncomfortableness, i.e. stiffness, produced by the adhesion thereof to the skin.

The porous plastic film usable in the present invention is exemplified by those made from polyethylene, polypropylene, polytetrafluoroethylene, ethylene/vinyl acetate copolymer, vinyl acetate/vinyl chloride copolymer, plastic vinyl chloride, polyurethane, poly(vinylidene chloride), polyester and the like. Of these, high molecular weight polyethylene, ultra high molecular weight polyethylene and the like are preferably used, which have sufficient resistance (e.g., non-swelling property and the like) to the above-mentioned organic liquid component.

The above-mentioned porous plastic film preferably has a porosity of about 20–60%, particularly 25–55%, for release control of the drug. It preferably has a pore size of not more than 50 μm, particularly 20–35 μm.

According to the present invention, the adhesive layer has a release-controlling layer. By this constitution, the release amount and the release rate can be controlled as aimed in the present invention, thereby achieving sustained percutaneous absorption of the drug into the body, and suppressing the irritation to the skin due to the drug. Specifically, the drug content of the adhesive layer B (skin contact side) is preferably controlled to not more than 200 μg/cm², particularly 75–150 μg/cm², and drug migration rate from the adhesive layer A (support side) to the adhesive layer B is preferably controlled to not more than 120 μg/cm²/t$^{1/2}$, particularly 70–120 μg/cm²/t$^{1/2}$.

Because the adhesive layer B is located on the skin contact side, the drug contained in the adhesive layer B is immediately released to the skin upon application. When the drug content of the adhesive layer B is too high, therefore, control of the release amount to the skin becomes difficult. Therefore, the drug content of the adhesive layer B is preferably set to not more than 200 μg/cm². In addition, the drug release rate from the adhesive layer B is preferably controlled to not more than 180 μg/cm²/t$^{1/2}$, particularly not more than 10–150 μg/cm²/t$^{1/2}$. The release rate can be controlled by adjusting the thickness and composition of the adhesive layer, the total content and concentration of the drug, and the organic liquid component content.

The drug contained in the adhesive layer A needs to pass the release-controlling layer before release to the skin, which relates to the sustained release. When the release-controlling layer permeation rate is too high, a large amount of drug is released to the skin in a short time and sustained release cannot be achieved. It is therefore preferable to control the drug migration rate from the adhesive layer A to the adhesive layer B to not more than 120 μg/cm²/t$^{1/2}$, particularly 70–120 μg/cm²/t$^{1/2}$. The migration rate can be controlled by adjusting the composition of the adhesive layer, and the material and thickness of the release-controlling layer.

The support to be used in the present invention is not subject to any particular limitation as long as it can hold the adhesive layer and improve adhesion performance. Examples thereof include plastic films made from polyester, polyethylene, polypropylene, poly(vinyl chloride), poly(vinylidene chloride), ethylene/vinyl acetate copolymer, cellulose acetate, ethyl cellulose, vinyl acetate/vinyl chloride copolymer, polyurethane and the like, paper, woven fabric, nonwoven fabric and laminates thereof, laminates of these and metal foil, and the like.

The above-mentioned support has a thickness that does not cause uncomfortableness when the percutaneously absorptive preparation of the present invention is adhered to the skin surface and that affords a mechanical strength sufficient to hold the preparation integrally upon peeling off from the skin surface. It is generally about 1–50 μm, preferably 1–30 μm According to the present invention, an adhesive layer containing the above-mentioned release-controlling layer is preferably formed directly or indirectly via a primer and the like formed for an improved anchor effect, on at least one side of the support, for the improvement of the handling property, adhesiveness to the skin, percutaneous absorption by the occlusive dressing technique and the like.

The percutaneously absorptive preparation of the present invention can be obtained as follows. A coating solution for an adhesive layer is applied to a release liner (e.g., film etc. after release treatment) and dried (formation of adhesive layer B). Separately, a coating solution for an adhesive layer is applied on a support and dried (formation of adhesive layer A). The adhesive layer B on the release liner and adhesive layer A on the support are respectively adhered to both sides of a release-controlling layer and the release liner is removed to give a percutaneously absorptive preparation having a structure of support/adhesive layer A/release-controlling layer/adhesive layer B.

While the shape of the percutaneously absorptive preparation of the present invention is not particularly limited, it is preferably a tape for superior operability.

EXAMPLES

The present invention is explained in detail in the following by referring to examples. The present invention is not limited by these examples in any way, but can be modified in various ways as long as they do not deviate from the technical conception of the present invention. In the following description, "parts" means "parts by weight" and % means wt %.

Example 1

Acrylic adhesive (75 parts, 2-ethylhexyl acrylate/acrylic acid copolymer, 2-ethylhexyl acrylate/acrylic acid=95/5 (weight ratio)) was dissolved in ethyl acetate. Thereto were added diethyl sebacate (20 parts) and betahistine in a free form (5 parts) to give a coating solution for adhesive layer. The above-mentioned coating solution was applied onto a polyester film after release treatment so that the thickness after drying would be 30 μm and dried (formation of adhesive layer B). Separately, the above-mentioned coating solution was applied on a support nonwoven fabric (laminate of a 6 μm thick polyester film and a polyester nonwoven fabric having a basis weight of 8 g/m²) so that the thickness after drying would be 60 μm and dried (formation of adhesive layer A).

As a release-controlling layer, a 50 μm thick high molecular weight porous polyethylene film (porosity:45%, polyethylene film manufactured by NITTO DENKO CORPORATION, trademark BREATHRON) was used. On both sides of the film were adhered adhesive layer B on the polyester film after release treatment and adhesive layer A on the support and the polyester film after release treatment was peeled off to give a percutaneously absorptive preparation having a constitution of support/adhesive layer A/release-controlling layer/adhesive layer B.

Example 2

A polyisobutylene adhesive (60 parts, a mixture of polyisobutylene (100 parts) having a viscosity-average molecular weight of 1,400,000 and polyisobutylene (100 parts) having a viscosity-average molecular weight of 60,000) was dissolved in hexane. Isopropyl myristate (30 parts) and betahistine in a free form (10 parts) were added to give a coating solution for adhesive layer. The above-mentioned coating solution was applied on a polyester film after release treatment so that the thickness after drying would be 20 μm and dried (formation of adhesive layer B). Separately, the above-mentioned coating solution was applied on a support nonwoven fabric (laminate of a 6 μm thick polyester film and a polyester nonwoven fabric having a basis weight of 8 g/m²) so that the thickness after drying would be 30 μm and dried (formation of adhesive layer A).

As a release-controlling layer, a 50 μm thick ultra high molecular weight porous polyethylene film (porosity:30%, ultra high molecular weight polyethylene film manufactured by NITTO DENKO CORPORATION, trademark SUN-MAP) was used. On both sides of the film were adhered adhesive layer B on the polyester film after release treatment and adhesive layer A on the support and the polyester film after release treatment was peeled off to give a percutaneously absorptive preparation having a constitution of support/adhesive layer A/release-controlling layer/adhesive layer B.

Comparative Example 1

A coating solution for adhesive layer as in Example 1 was prepared and the above-mentioned coating solution was applied on a support nonwoven fabric as in Example 1 so that the thickness after drying would be 90 μm and dried to give a percutaneously absorptive preparation having a constitution of support/adhesive layer.

Comparative Example 2

An acrylic adhesive (95 parts, 2-ethylhexyl acrylate/acrylic acid copolymer, 2-ethylhexyl acrylate/acrylic acid=95/5 (weight ratio)) was dissolved in ethyl acetate and betahistine (5 parts) in a free form was added to give a coating solution for adhesive layer. The solution was applied on a support nonwoven fabric as in Example 1 so that the thickness after drying would be 90 μm and dried to give a percutaneously absorptive preparation having a constitution of support/adhesive layer.

Comparative Example 3

A coating solution for adhesive layer as in Example 2 was prepared and the above-mentioned coating solution was applied on a support nonwoven fabric as in Example 2 so that the thickness after drying would be 50 μm and dried to give a percutaneously absorptive preparation having a constitution of support/adhesive layer.

Comparative Example 4

A polyisobutylene adhesive (90 parts, a mixture of polyisobutylene (100 parts) having a viscosity-average molecular weight of 1,400,000 and polyisobutylene (100 parts) having a viscosity-average molecular weight of 60,000) was dissolved in hexane. Betahistine in a free form (10 parts) was added to give a coating solution for adhesive layer. The above-mentioned coating solution was applied on a support nonwoven fabric so that the thickness after drying would be 50 μm and dried to give a percutaneously absorptive preparation having a constitution of support/adhesive layer.

The percutaneously absorptive preparations obtained in Examples 1–2 and Comparative Examples 1–4 were subjected to the following tests.

Test Example 1

Releasability Test

The percutaneously absorptive preparations obtained in the above-mentioned respective Examples and Comparative Examples were punched out in 10 cm² circles and subjected to the underwater release test according to the Japan Pharmacopoeia, Dissolution Test Method 2 (puddle method). The results are shown in FIG. 1. The results in FIG. 1 clearly show that the presence of a release-controlling layer in an adhesive layer results in desired control of the drug release pattern.

Test Example 2

Skin Irritation Test

The percutaneously absorptive preparations obtained in the above-mentioned respective Examples and Comparative Examples were punched out in 10 cm² circles and adhered to the back of Wistar rat (8-week-old), whose skin surface had undergone cutting hair, shaving and cleaning. At 18 h after adhesion, the preparation was peeled off and the presence or otherwise of the stimulation at the part where the adhesive was applied due to the drug was evaluated according to the criteria of Draize et al. The results are shown in Table 1. The evaluation criteria are as follows.

<Irritation to the Skin>
O: no irritation to the skin
Δ: weak irritation to the skin
x: irritation to the skin of a moderate level or above Test Example 3

Permeability Through Snake Skin

The percutaneously absorptive preparations obtained in the above-mentioned respective Examples and Comparative Examples were punched out in 6 cm diameter circles and adhered to one surface of the skin of reticulate python. The side of the skin of the reticulate python without the percutaneously absorptive preparation was set on a 6 mm diameter diffusion cell and the amount of the drug permeated into the diffusion cell was measured to evaluate permeability. The amount of the drug permeated was measured by HPLC, and the permeation amount per unit area (24 h accumulation) and the maximum drug permeation rate per unit area were calculated. The results are shown in Table 1.

TABLE 1

|  | Irritation to the skin | Permeation amount ($\mu g/cm^2$) (24 h accumulation) | Maximum permeation rate ($\mu g/cm^2/h$) |
| --- | --- | --- | --- |
| Ex. 1 | o | 380 | 18.5 |
| Com. Ex. 1 | x | 410 | 63.0 |
| Com. Ex. 2 | o | 105 | 5.2 |
| Ex. 2 | o | 200 | 15.0 |
| Com. Ex. 3 | x | 220 | 65.0 |
| Com. Ex. 4 | o | 100 | 7.5 |

As is evident from the results of the above-mentioned Table 1, the preparations of Examples 1–2 scarcely showed irritation to the skin due to the drug and were free of practical problem in terms of drug permeability. In contrast, the preparations without a release-controlling layer of Comparative Examples 1–4 were practically unsatisfactory in terms of irritation to the skin due to the drug and permeability. The preparations of Comparative Examples 1 and 3 contained an organic liquid component but did not have a release-controlling layer. As a result, the drug showed greater maximum permeation rate, causing irritation to the skin due to the drug. The preparations of Comparative Examples 2 and 4 did not have a release-controlling layer but the amount of drug permeation was small due to the absence of an organic liquid component.

As is evident from the foregoing explanation, the present invention can provide a percutaneously absorptive preparation, which affords sustained percutaneous absorption of drug to exert a desired pharmacological effect for a long time. In addition, the preparation of the present invention can establish percutaneous absorbability and low skin irritation, wherein the irritation to the skin due to the drug is suppressed.

This application is based on patent application No. 2000-268899 filed in Japan, the contents of which are hereby incorporated by reference.

What is claimed is:

1. A percutaneously absorptive preparation comprising a support and an adhesive layer having a release-controlling layer, which is formed at least on one side of the support,
    wherein the adhesive layer contains an adhesive and 0.5–60 wt % of a drug, except 1,2-ethanediol derivatives,
    wherein the drug is formulated in the adhesive,
    wherein the adhesive layer having a release-controlling layer has a laminate structure consisting of adhesive layer A/release-controlling layer/adhesive layer B from the support side, and
    wherein the release-controlling layer is a porous plastic film comprising an ultra high molecular weight polyethylene.

2. The percutaneously absorptive preparation of claim 1, wherein the adhesive is at least one member selected from the group consisting of an acrylate adhesive comprising, as a main component, a polymer containing $C_{2-18}$ alkyl (meth) acrylate in a proportion of not less than 40 wt % as a polymerization component; a rubber adhesive comprising at least one member selected from polyisobutylene, polyisoprene and styrene-diene-styrene copolymer as a main component; and a silicone adhesive comprising polyorganosiloxane containing a dimethylsiloxane unit as a main component.

3. The percutaneously absorptive preparation of claim 1, wherein the adhesive layer comprises at least one organic liquid component selected from the group consisting of glycols, fats and oils, fatty acids, alcohols and fatty acid esters.

4. The percutaneously absorptive preparation of claim 1, wherein the adhesive is a rubber adhesive comprising polyisobutylene as a main component and the adhesive layer further contains a lower alkyl ester of a higher fatty acid.

5. The percutaneously absorptive preparation of claim 1, wherein the porous plastic film has a porosity of 20–60%.

6. The percutaneously absorptive preparation of claim 2, wherein the porous plastic film has a porosity of 20–60%.

7. The percutaneously absorptive preparation of claim 1, wherein the adhesive layer B has a drug content of not more than 200 $\mu g/cm^2$.

* * * * *